| | | | |
|---|---|---|---|
| United States Patent [19] | | [11] | 3,976,590 |
| Yax et al. | | [45] Aug. 24, 1976 |  |

[54] MIXTURE OF HOMOLOGUE ANHYDRIDES OF TETRA-HYDROPHTHALIC ANHYDRIDE AND THE PROCESS FOR OBTAINING SAME

[76] Inventors: Emile Yax, 11, rue Jeanne d'Arc,, Petite-Rosselle, Moselle, France; Mechthild Zander, Rotenbergstrasse 36, Sarrebruck, Germany

[22] Filed: Aug. 26, 1974

[21] Appl. No.: 500,738

[30] Foreign Application Priority Data
Aug. 27, 1973  France .................................. 73.30957

[52] U.S. Cl. ............................ 252/182; 260/346.6; 260/346.7
[51] Int. Cl.² .................. C09K 3/00; C07D 307/89; C07D 307/93
[58] Field of Search ........... 260/346.7, 346.3, 346.6; 252/182

[56] References Cited
UNITED STATES PATENTS

| | | | |
|---|---|---|---|
| 3,245,916 | 4/1966 | Woskow | 252/182 |
| 3,247,125 | 4/1966 | Woskow | 252/182 |
| 3,326,941 | 6/1967 | Campagne | 260/346.7 |
| 3,341,555 | 9/1967 | Wooster | 260/346.3 |
| 3,580,857 | 5/1971 | Cheng | 252/182 |
| 3,580,858 | 5/1971 | Evans | 252/182 |
| 3,600,356 | 8/1971 | Murai | 252/182 |
| 3,647,701 | 3/1972 | Robinson | 252/182 |
| 3,691,083 | 9/1972 | Niklaus | 252/182 |
| 3,775,335 | 11/1973 | Irwin | 252/182 |

*Primary Examiner*—Samuel W. Engle
*Assistant Examiner*—Donald P. Walsh
*Attorney, Agent, or Firm*—Karl W. Flocks

[57] ABSTRACT

A mixture of anhydrides homologous to tetra-hydrophthalic anhydride, having a melting point between 40° and 50°C, and comprising from 30 to 50 % of endo-methylene-tetrahydrophthalic anhydride, from 30 to 45 % of methyl-4-tetrahydrophthalic anhydride and from 10 to 25 % of methyl-3-tetrahydrophthalic anhydride and is obtained by the reaction in counter-flow of maleic anhydride with a petrochemical C5 fraction, containing cyclopentadiene, isoprene and piperylene in substantially the same amount, together with other unsaturated C5 hydrocarbon fractions, selected from the group comprising the fractions derived from steam-cracking and pyrolysis of naphtha, the control of the conditions of temperature and flow-rate in order to have an essentially complete reaction, and the recovery of the resulting mixture of anhydrides.

8 Claims, No Drawings

MIXTURE OF HOMOLOGUE ANHYDRIDES OF TETRA-HYDROPHTHALIC ANHYDRIDE AND THE PROCESS FOR OBTAINING SAME

FIELD OF INVENTION

The present invention relates to a process for preparing homologue anhydrides of tetra-hydrophthalic anhydride by the action of maleic anhydride on a mixture of C5 hydrocarbons containing as reactant constituents, cyclo-pentadiene, isoprene and trans piperylene, together with other saturated ethylene and diene hydrocarbons. It also relates to the mixture of anhydrides of low-melting point obtained by this process and its applications in the field of thermo-setting compounds, especially serving as hardeners for epoxy resins.

BACKGROUND

It is already known to react liquid maleic anhydride with each of the three dienes referred to above. These reactions take place with almost a quantitative yield and result respectively, in endomethylene-tetra-hydrophthalic anhydride, the anhydride of bicyclo, (2,2,1) heptene-5 dicarboxylic-2,3 acid from cyclo-pentadiene, in methyl-4-tetra-hydrophthalic anhydride from isoprene and in methyl-3-tetra-hydrophthalic anhydride from piperylene-trans.

More recently, mixtures have been obtained of methyltetra-hydrophthalic anhydrides from mixtures previously freed from cyclo-pentadiene, or at least impoverished in this hydrocarbon. It is in fact difficult to react quantitatively in the same operation, dienes of such different reactivities as cyclopentadiene, isoprene and piperylene. Furthermore, in the methods of the prior art, when the starting mixtures contained cis piperylene as well as certain ethylene hydrocarbons, the product obtained was contaminated with polymerization products of these hydrocarbons or with co-polymerization products of these hydrocarbons with maleic anhydride, which makes it necessary to work in an inert atmosphere in the presence of a free-radical inhibitor and to purify the product obtained.

SUMMARY

A continuous method has now been developed permitting a practically complete exhaustion of the reactant dienes of a mixture of C5 hydrocarbons such as a distillation fraction of a pyrolysis gasoline or steam cracking of naphtha containing a substantial quantity, e.g. of the order of 50 %, of reactant dienes, the amounts of cyclo-pentadiene, isoprene and piperylene being substantially the same, with a negligible formation of by-products and resulting in a mixture of anhydrides which is directly utilizable in the field of thermo-settings.

DETAILED DESCRIPTION OF EMBODIMENTS

The process according to the invention consists in circulating, in a counter-flow reactor, the molten maleic anhydride and the C5 fraction at a temperature between 100° and 130°C, regulating the conditions of flow and, if needed, the temperatures in such manner that only very little reactant dienes are left in the C5 fraction at the outlet, which corresponds to the reaction of at least the stoichiometric quantity of maleic anhydride with respect to the whole of the dienes present, collecting the mixture of anhydrides thus formed and, if so required, degasifying this mixture, for example by heating to 160°–180°C.

It has been found that under these conditions, practically no polymerization and co-polymerization products of the unsaturated hydrocarbons was formed, even in the absence of a free-radical inhibitor.

The product thus obtained, containing in general from 30 to about 50 % of endo-methylene-tetra-hydrophthalic anhydride, from 30 to 45% of methyl-4-tetra-hydrophthalic anhydride and 10 to 25 % of methyl-3-tetra-hydrophthalic anhydride, has a melting point of between 40° and 60°C, which makes its utilization advantageous as a hardener in the field of epoxy resins.

This melting point may furthermore be still further reduced by mixing the product with other anhydrides having a low melting point, such as hexahydrophthalic anhydride. In addition, these anhydrides mixed with a liquid epoxy resin of low epoxy equivalent, for example of an epoxy equivalent of 200, gives a product having a viscosity lower than that of the two components and which may be stored for a period of several months without becoming gelified.

EXAMPLE OF PREPARATION

There is utilized a C5 fraction obtained from steam-cracking and containing about 50 % of reactant dienes with 19.38 % of isoprene, 12.87 % of piperylene and 18.51 % of cyclo-pentadiene.

A reactor, constituted by a stainless steel tube having an internal diameter of 38 mm and a length of 2,000 mm provided with a double wall and heat-insulated externally, is supplied at the head with melted maleic anhydride at a flowrate of 430 grams per hour and at the foot with the C5 fraction at a flow-rate of 748 grams per hour. The reaction is started by circulation of expanded steam at about 102°C in the double wall and it is carried out at a practically constant temperature by removing part of the reaction heat by vaporization of the C5. The temperature of the reactor (measured at the lower third) becomes stabilized at about 102°–105°C, (slightly above the temperature of the double wall).

The flow of the crude product (mixture of anhydrides) is effected either by extraction with a pump or by a system of syphoning, taking advantage in this latter case of the difference in pressure head between the liquid charged with bubbles from the reactor and the liquid from the syphon. There are obtained 722 grams per hour of a mixture of anhydrides which, after degasifying at 180°C for 2 hours, has a melting point of 50°–60°C. This mixture contains less than 1 % of maleic anhydride. Its acid number is 680 and its content of free acid is 1.2 %. It contains less than 1.5 % of non-distillable products and the chromatographic analysis of the distillable fraction shows the following composition:

| | |
|---|---|
| Endomethylene-tetra-hydrophthalic anhydride | 45.40 % |
| Methyl-4-tetra-hydrophthalic anhydride | 39.65 % |
| Methyl-3-tetra-hydrophthalic anhydride | 13.43 % |
| Other isomers of methyl-tetra-hydrophthalic anhydride | 0.54 % |
| Light constituents and non-identified constituents | 0.98 % |

Furthermore, the balance sheet of the dienes at the inlet and outlet of the reactor is as follows:

|  | Inlet | Outlet |
|---|---|---|
| Flow-rate (g/h) | 748 | 418 |
| Constituents (%) | | |
| Isoprene | 19.38 | 4.45 |
| Piperylene | 12.87 | 10.15 |
| Cyclo-pentadiene | 18.51 | — |
| Total dienes | 50.76 | 14.60 |

The isoprene is dosed in the C5 outlet fraction for following the reaction and controlling the flow-rate.

The reaction can of course deliberately be made incomplete if it is desired to employ part of the isoprene and the piperylene for a different use, or on the contrary to impoverish slightly the initial mixture in cyclo-pentadiene by dimerizing a part of this latter in a manner known per se.

EXAMPLE OF APPLICATION

There was employed a mixture obtained by the process according to the invention, containing about 35 % of endomethylene tetra-hydrophthalic anhydride and 65 % of methyl-3 and 4-tetra-hydrophthalic anhydrides.

90 parts by weight of this mixture are taken to 100 parts by weight of an epoxy resin having an epoxy equivalent of about 200 and a viscosity of about 120 poises at 25°C. The new mixture thus obtained had a viscosity of 16 poises at 25°C, and remained liquid during the whole period of storage at that temperature. It was still liquid at the end of three months and its viscosity was then 33 poises.

Two tests were carried out, at 25°C and at 150°C in the presence of a tertiary amine accelerator.

At 25°C, this composition gelified at the end of one month with 0.3 part of accelerator to 100 parts of resin.

At 150°C, a gel time of between 16 minutes and 2 minutes was obtained for proportions of accelerator comprised respectively between 0.1 and 1 part to 100 parts of resin, and in particular, a gel time of 9 minutes for 0.3 part of accelerator.

It will of course be understood that the present invention has only been described purely by way of explanation and not in any restrictive sense, and that any useful modification may be made thereto without thereby departing from its scope, as defined by the appended claims.

We claim:

1. A process for obtaining a mixture of anhydrides homologous to tetrahydrophthalic anhydride, having a melting point between 40° and 60°C and consisting essentially of from 30 to 50 % of endo-methylene-tetrahydrophthalic anhydride, from 30 to 45 % of methyl-4-tetrahydrophthalic anhydride and from 10 to 25 % of methyl-3-tetrahydrophthalic anhydride, comprising reacting maleic anhydride with a petro-chemical C5 fraction, containing on the order of about 50 % of reactant dienes comprising essentially cyclopentadiene, isoprene and piperylene in substantially the same amount, together with other unsaturated C5 hydrocarbon fractions, selected from the group comprising the fractions derived from steam-cracking and pyrolysis of naptha, by passing said maleic anhydride counter-current to said petrochemical C5 fraction, controlling the conditions of temperature between 100° and 130°C and of flow-rate to provide an essentially complete reaction, and recovering the resulting mixture of anhydrides.

2. A process as claimed in claim 1, in which the conditions of flow-rate are controlled in such a manner as to react at least the stoichiometric quantity of maleic anhydride, with respect to the whole of the dienes being reacted.

3. A process as claimed in claim 1, in which a reactor is fed at the column head by maleic anhydride, at the column foot with the C5 fraction and the mixture of anhydride is collected from the column foot and the exhausted C5 fraction at the column head.

4. A process as claimed in claim 1, in which the mixture of anhydrides obtained is degasified by heating.

5. A process as claimed in claim 4, in which the heating is effected at between 160° and 180°C.

6. A process in accordance with claim 1 wherein said reaction is effected in the absence of an inert atmosphere.

7. A process in accordance with claim 6 wherein said reaction is effected in the absence of a free-radical inhibitor.

8. A process for obtaining a mixture of anhydrides homologous to tetrahydrophthalic anhydride, having a melting point between 40° and 60°C and consisting essentially of from 30 to 50 % of endo-methylene-tetrahydrophthalic anhydride, from 30 to 45 % of methyl-4-tetrahydrophthalic anhydride and from 10 to 25 % of methyl-3-tetrahydrophthalic anhydride, comprising reacting maleic anhydride with a petro-chemical C5 fraction, containing on the order of about 50 % of a mixture of cyclopentadiene, isoprene and piperylene in substantially the same amount, said reaction being effected by passing said maleic anhydride counter-current to said petrochemical C5 fraction in the absence of an inert atmosphere and in the absence of a free-radical inhibitor, controlling the conditions of temperature between 100° and 130°C and of flow-rate to provide an essentially complete reaction, and recovering the resulting mixture of anhydrides.

* * * * *